United States Patent
Prisco et al.

(10) Patent No.: US 10,820,949 B2
(45) Date of Patent: Nov. 3, 2020

(54) MEDICAL ROBOTIC SYSTEM WITH DYNAMICALLY ADJUSTABLE SLAVE MANIPULATOR CHARACTERISTICS

(75) Inventors: Giuseppe Prisco, Mountain View, CA (US); Hubert Stein, San Francisco, CA (US); Paul Millman, San Jose, CA (US); David Bailey, Redwood City, CA (US); William Nowlin, Los Altos, CA (US); Michael Ikeda, Saratoga, CA (US); Thomas Nixon, Santa Clara, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 1529 days.

(21) Appl. No.: 11/847,168

(22) Filed: Aug. 29, 2007

(65) Prior Publication Data

US 2009/0062813 A1 Mar. 5, 2009

Related U.S. Application Data

(60) Continuation-in-part of application No. 11/074,372, filed on Mar. 7, 2005, now Pat. No. 7,373,219, which
(Continued)

(51) Int. Cl.
*A61B 34/30* (2016.01)
*A61B 34/37* (2016.01)
*A61B 90/00* (2016.01)

(52) U.S. Cl.
CPC .............. *A61B 34/30* (2016.02); *A61B 34/37* (2016.02); *A61B 90/361* (2016.02)

(58) Field of Classification Search
CPC ... B25J 9/06; B25J 9/1615; B25J 18/00; B25J 9/107; B25J 17/0208; B25J 9/1692;
(Continued)

(56) References Cited

U.S. PATENT DOCUMENTS 4,510,574 A 4/1985 Guittet et al.
4,553,746 A 11/1985 Lee
(Continued)

FOREIGN PATENT DOCUMENTS

DE 4213426 1/1997
WO WO-199216141 10/1992
(Continued)

OTHER PUBLICATIONS

Vertut, Jean and Philippe Coiffet, *Teleoperation and Robotics: Evolution and Development*, English translation Prentice-Hall, Inc., Inglewood Cliffs, NJ, USA, 1986, 332 pages.
(Continued)

*Primary Examiner* — Stephen Holwerda

(57) ABSTRACT

A slave manipulator manipulates a medical device in response to operator manipulation of an input device through joint control systems. The stiffness and strength of the slave manipulator are adjustable according to criteria such as the mode of operation of the slave manipulator, the functional type of the medical device currently being held by the slave manipulator, and the current phase of a medical procedure being performed using the slave manipulator by changing corresponding parameters of the control system. For safety purposes, such changes are not made until it is determined that it can be done in a smooth manner without causing jerking of the medical device. Further, an excessive force warning may be provided to surgery staff when excessive forces are being commanded on the slave manipulator for more than a specified period of time.

22 Claims, 9 Drawing Sheets

Related U.S. Application Data is a continuation of application No. 10/437,771, filed on May 13, 2003, now Pat. No. 6,879,880, which is a division of application No. 09/544,153, filed on Apr. 6, 2000, now Pat. No. 6,594,552.

(60) Provisional application No. 60/128,157, filed on Apr. 7, 1999.

(58) Field of Classification Search
CPC ........ B25J 19/0091; B25J 9/104; B25J 9/046; B25J 18/002; B25J 9/1633; B25J 3/04; B25J 9/1689; B23Q 11/0014; A61B 18/14; A61B 19/22; A61B 17/32056; A61B 18/24; A61B 19/2203; A61B 17/11
USPC ........ 606/130; 700/245, 260; 901/30, 31, 33
See application file for complete search history.

(56) References Cited

U.S. PATENT DOCUMENTS

| | | | |
|---|---|---|---|
| 4,627,169 A * | 12/1986 | Zafred | B23Q 1/36 33/520 |
| 4,696,501 A | 9/1987 | Webb | |
| 4,756,662 A * | 7/1988 | Tanie | B25J 9/06 414/729 |
| 4,791,588 A | 12/1988 | Onda et al. | |
| 4,819,978 A | 4/1989 | Scheinman et al. | |
| 4,842,475 A * | 6/1989 | Driels | B23P 19/105 414/730 |
| 4,921,393 A * | 5/1990 | Andeen | B23Q 11/0014 414/729 |
| 4,979,949 A * | 12/1990 | Matsen, III | A61B 17/15 606/53 |
| 5,068,018 A * | 11/1991 | Carlson | 204/554 |
| 5,086,401 A * | 2/1992 | Glassman et al. | 700/259 |
| 5,105,367 A * | 4/1992 | Tsuchihashi | B25J 3/04 700/264 |
| 5,125,759 A * | 6/1992 | Chun | B25J 17/0208 403/220 |
| 5,184,601 A | 2/1993 | Putman | |
| 5,206,930 A * | 4/1993 | Ishikawa | B25J 9/1633 318/568.18 |
| 5,250,056 A | 10/1993 | Hasson | |
| 5,321,874 A | 6/1994 | Mills et al. | |
| 5,339,799 A * | 8/1994 | Kami | A61B 18/14 600/109 |
| 5,341,459 A * | 8/1994 | Backes | B25J 9/1661 700/260 |
| 5,354,162 A | 10/1994 | Burdea et al. | |
| 5,444,343 A * | 8/1995 | Enomoto | G05B 19/4141 318/567 |
| 5,503,320 A | 4/1996 | Webster et al. | |
| 5,513,100 A * | 4/1996 | Parker | G05B 19/427 318/568.18 |
| 5,572,684 A | 11/1996 | Canik et al. | |
| 5,626,595 A * | 5/1997 | Sklar | A61B 17/320016 606/170 |
| 5,637,108 A | 6/1997 | Vidal et al. | |
| 5,696,837 A | 12/1997 | Green | |
| 5,697,939 A | 12/1997 | Kubota et al. | |
| 5,762,458 A * | 6/1998 | Wang | A61B 17/11 414/1 |
| 5,784,542 A | 7/1998 | Ohm et al. | |
| 5,792,135 A | 8/1998 | Madhani et al. | |
| 5,792,178 A | 8/1998 | Welch et al. | |
| 5,800,423 A | 9/1998 | Jensen | |
| 5,807,377 A * | 9/1998 | Madhani | A61B 34/77 606/1 |
| 5,808,665 A * | 9/1998 | Green | 348/65 |
| 5,841,950 A | 11/1998 | Wang et al. | |
| 5,855,553 A | 1/1999 | Tajima et al. | |
| 5,859,934 A | 1/1999 | Green | |
| 5,876,325 A | 3/1999 | Mizuno et al. | |
| 5,898,599 A * | 4/1999 | Massie | B25J 9/1689 318/628 |
| 5,931,832 A | 8/1999 | Jensen | |
| 5,949,686 A | 9/1999 | Yoshinada et al. | |
| 6,002,184 A | 12/1999 | Delson et al. | |
| 6,024,695 A | 2/2000 | Taylor et al. | |
| 6,113,395 A | 9/2000 | Hon | |
| 6,127,792 A | 10/2000 | Kamiya et al. | |
| 6,165,184 A | 12/2000 | Verdura et al. | |
| 6,219,032 B1 | 4/2001 | Rosenberg et al. | |
| 6,219,589 B1 | 4/2001 | Faraz et al. | |
| 6,223,100 B1 | 4/2001 | Green | |
| 6,228,097 B1 | 5/2001 | Levinson et al. | |
| 6,231,526 B1 | 5/2001 | Taylor et al. | |
| 6,236,906 B1 | 5/2001 | Mueller | |
| 6,244,809 B1 | 6/2001 | Wang et al. | |
| 6,259,806 B1 | 7/2001 | Green | |
| 6,280,458 B1 | 8/2001 | Boche et al. | |
| 6,312,435 B1 | 11/2001 | Wallace et al. | |
| 6,317,651 B1 | 11/2001 | Gerstenberger et al. | |
| 6,323,837 B1 | 11/2001 | Rosenberg | |
| 6,325,808 B1 | 12/2001 | Bernard et al. | |
| 6,331,181 B1 | 12/2001 | Tierney et al. | |
| 6,424,885 B1 | 7/2002 | Niemeyer et al. | |
| 6,451,027 B1 | 9/2002 | Cooper et al. | |
| 6,459,926 B1 | 10/2002 | Nowlin et al. | |
| 6,468,265 B1 | 10/2002 | Evans et al. | |
| 6,491,701 B2 | 12/2002 | Tierney et al. | |
| 6,505,085 B1 | 1/2003 | Tuttle et al. | |
| 6,594,552 B1 | 7/2003 | Nowlin et al. | |
| 6,764,445 B2 | 7/2004 | Ramans et al. | |
| 6,879,880 B2 | 4/2005 | Nowlin et al. | |
| 7,373,219 B2 | 5/2008 | Nowlin et al. | |
| 7,714,836 B2 | 5/2010 | Rodomista et al. | |
| 7,778,733 B2 | 8/2010 | Nowlin et al. | |
| 2001/0018591 A1 | 8/2001 | Brock et al. | |
| 2001/0040439 A1 | 11/2001 | Kato et al. | |
| 2001/0056283 A1 | 12/2001 | Carter et al. | |
| 2002/0042620 A1 | 4/2002 | Julian et al. | |
| 2002/0045905 A1 | 4/2002 | Gerbi et al. | |
| 2002/0058929 A1 | 5/2002 | Green | |
| 2003/0006669 A1 * | 1/2003 | Pei et al. | 310/309 |
| 2003/0195664 A1 * | 10/2003 | Nowlin et al. | 700/260 |
| 2005/0149003 A1 | 7/2005 | Tierney et al. | |
| 2006/0178559 A1 | 8/2006 | Kumar et al. | |
| 2006/0241414 A1 | 10/2006 | Nowlin et al. | |
| 2007/0012135 A1 | 1/2007 | Tierney et al. | |
| 2009/0234371 A1 | 9/2009 | Tierney et al. | |
| 2017/0144302 A1 | 5/2017 | Rohmer et al. | |

FOREIGN PATENT DOCUMENTS

| | | |
|---|---|---|
| WO | WO-9313916 A1 | 7/1993 |
| WO | WO-199501757 | 1/1995 |
| WO | WO-9950721 A1 | 10/1999 |
| WO | WO-0141052 A1 | 6/2001 |

OTHER PUBLICATIONS

Alexander, Arthur D. III, "Impacts of Telemation on Modern Society," Symposium on Theory and Practice of Robots and Manipulators, Centre for Mechanical Sciences 1st CISM IFToMM Symposium, Sep. 5-8, 1974, pp. 121-136, vol. 2, Springer-Verlag.

Bauer, W. et al., "Virtual reality as interface for interaction and manipulation in endoscopy," Minimally Invasive Therapy, 1995, pp. 319-339, vol. 4, Blackwell Science Ltd.

Bejczy, Antal K. et al., "Controlling Remote Manipulators through Kinesthetic Coupling," Computers in Mechanical Engineering, 1983, pp. 48-60, vol. 1—Issue 1.

Bergamasco M., et al., "Advanced Interfaces for Teleoperated Biomedical Robots," IEEE Engineering in Medicine & Biology Society 11th Annual Int'l Conf., pp. 912-913, vol. 3, IEEE, Jun. 1989.

Bluethmann, B et al., "Experiments in Dexterous Hybrid Force and Position Control of Master/Slave Electrohydraulic Manipulator," in Proceedings of the 1995 IEEE/RSJ International Conference on

(56) References Cited

OTHER PUBLICATIONS

Intelligent Robots and Systems, Aug. 5-9, 1995, pp. 27-32, vol. 3, IEEE Computer Society.

Bowersox, Jon C. et al., "Vascular applications of telepresence surgery: Initial feasibility studies in swine," J. Vascular Surgery, Feb. 1996, pp. 281-287, vol. 23—Issue 2.

Butner, Steven E. et al., "A real-time system for tele-surgery," IEEE 21st International Conference on Distributed Computing Systems, 2001, pp. 236-243, IEEE.

Cavusoglu, Murat Cenk et al., "A Laparoscopic Telesurgical Workstation," IEEE Transactions on Robotics and Automation, Aug. 1999, vol. 15, Issue 4, pp. 728-739.

Fischer, Harald et al., "Tactile Feedback for Endoscopic Surgery," Interactive Technology and the New Paradigm for Healthcare, 1995, pp. 114-117, vol. 19, IOS Press and Ohmsha.

Goertz, Ray et al., "ANL mark E4A electric master slave manipulator," Proc 14th Conf. on Remote System Technology, 1966, pp. 115-123.

Hannaford, Blake et al., "Computerized endoscopic surgical grasper," Proceedings, Medicine Meets Virtual Reality, San Diego, CA., 1998, 7 pages, IOS Press.

Hill, John W., "Telepresence surgery demonstration system," Robotics and Automation, 1994, pp. 2302-2307, vol. 3, SRI International.

Howe, Robert D. et al., "Robotics for Surgery," Annu. Rev. Biomed. Eng, 1999, pp. 211-242, vol. 1.

Jackson, Bernie G. et al., "Force Feedback and Medical Simulation," Interactive Technology and the New Paradigm for Healthcare, Morgan et al. (Eds ), 1995, pp. 147-151, vol. 24, IOS Press and Ohms.

Kazerooni, H., "Design and analysis of the statically balanced direct-drive robot manipulator," Robotics and Computer-Integrated Manufacturing, 1989, pp. 287-293, vol. 6, Issue 4.

Kim, Won S. et al., "Remote Robot Control with High Force Feedback Gain," Technical Support Package NASA Tech Brief JPL New Technology Report NPO 18668, Aug. 1993, vol. 17—Issue 8, 44 pages.

Komatsu, Tadashi et al., "Control of a space flexible master slave manipulator based on parallel compliance models," IEEE International Conference on Robotics and Automation, 1998, pp. 1932-1937, vol. 3, IEEE.

Lai, Fuji et al., "Evaluating control modes for constrained robotic surgery," IEEE International Conferenceon Robotics & Automation San Francisco, Apr. 2000, vol. 1, pp. 603-609, IEEE.

Lorenz, Robert D. et al., "A Direct Drive Robot Parts and Tooling Gripper with High Performance Force Feedback Control," IEEE Transactions on Industry Applications, Mar./Apr. 1991, pp. 275-281, vol. 27—Issue 2, IEEE.

Mack, Michael J. et al., "Minimally Invasive and Robotic Surgery," JAMA, 2001, pp. 568-572, vol. 285—Issue 5.

Noonan, David, "The Ultimate Remote Control," Newsweek, Jun. 25, 2001, 7 pages total.

Parsell, D.L., "Surgeons in U.S. perform operation in France via robot," National Geographic News, Sep. 19, 2001, pp. 1-5.

Rosen, Jacob, et al., "Force controlled and teleoperated endoscope grasper for minimally invasive surgery," IEEE Experimental Performance Evaluation, IEEE, 1999, vol. 46, Issue 10, pp. 1212-1221.

Rotnes, Jan Sigurd et al., "Digital trainer developed for robotic assisted cardiac surgery," Studies in health technology and informatics, 2001, vol. 81, pp. 424-430.

Sabatini, A. M. et al., "Force Feedback Based Telemicromanipulation for Robot Surgery on Soft Tissue," IEEE Engineering in Medicine and Biology Society 11th Annual International Conference, 1989, pp. 890-891, vol. 3, IEEE.

Satava, Richard M., "Emerging technologies for surgery in the 21st century," Arch Surg, 1999, pp. 1197-1202, vol. 134.

Schaaf, Tracy A., "Robotic surgery: The future is now," Medical Device Link, Mar./Apr. 2001, pp. 1-13 Internet http://www.devicelink.com/mx/archive/01/03/0103mx024.html.

Schenker, Paul S. et al., "Development of a Telemanipulator for Dexterity Enhanced Microsurgery," 2nd Annual International Symposium on Medical Robotics and Computer Assisted Surgery, Nov. 4-7, Baltimore, Maryland, 1995, pp. 81-88.

Sharpe, J.E.E., "Human factors in the use of covariant bilateral manipulators," Ch. 24 Robot Control Theory and Applications Warwick K. and Pugh A. (Eds.) Peter Peregrinus Ltd. on behalf of the Institution of Electrical Engineers, Dec. 1988, pp. 219-236.

Spain, Edward H., "Stereo Advantage for a Peg in Hole Task Using a Force Feedback Manipulator," SPIE Stereoscopic Displays and Applications, 1990, pp. 244-254, vol. 1256, IEEE.

Sukthankar, Sujat M. et al., "Force Feedback Issues in Minimally Invasive Surgery," Interactive Technology and the New Paradigm for Healthcare, 1995, pp. 375-379, vol. 56, IOS Press and Ohmsha.

Sukthankar, Sujat M. et al., "Towards force feedback in laparoscopic surgical tools," IEEE Human Interface Laboratory Dept. of Biomedical Engineering, Ohio, 1994, pp. 1041-1042, IEEE.

Taubes, Gary et al., "Surgery in Cyberspace," Discover magazine, Dec. 1994, vol. 15, issue 12, pp. 85-92.

Taylor, Russell H. et al., "A Telerobotic Assistant for Laparoscopic Surgery," IEEE Engineering in Medicine and Biology, May/Jun. 1995, pp. 279-288, vol. 14, Issue 3, IEEE.

Taylor, Russell H. et al., "Taming the Bull: Safety in a Precise Surgical Robot," Fifth International Conference on Advanced Robotics (91 ICAR), Jun. 19-22, 1991, vol. 1, pp. 865-870, IEEE.

Tendick Frank, et al., "Analysis of the Surgeon's Grasp for Telerobotic Surgical Manipulation," IEEE 11th Annual Int Conf on Engineering in Medicine and Biology, Jun. 1989, pp. 914-915, IEEE.

Thring, M.W., Robots and Telechirs: Manipulators with Memory; Remote Manipulators; Machine Limbs for the Handicapped, 1983, pp. 9-11, 108-131, 194-195, 235-279; Ellis Horwood Limited, Chapter 5,7,8,9.

Willett, Edward, "Telesurgery," 2001, pp. 1-3. Internet http://www.edwardwillet.com/Columns/telesurgery.htm.

Yokokohji, Yasuyoshi et al., "Bilateral Control of Master-Slave Manipulators for Ideal Kinesthetic Coupling—Formulation and Experiment-," Robotics and Automation, Proc. of IEEE International Conference on Robotics and Automation, May 12-14, 1992, pp. 849-858, vol. 1, IEEE.

\* cited by examiner

| Phase of Medical Procedure (Medical Device) | Adjustable Characteristic | Comments |
|---|---|---|
| Mechanical energy delivery (hydrojet, drill, saw, vacuum) | Stiffness | For "mechanical" surgical cutting devices a high stiffness would be desirable to avoid "kickback" off the tissue to be cut. For vacuum suction eventually a lower stiffness would be advantageous to have an instrument or device conform to a tissue or organ structure/surface. |
| Guidance (catheter, endoscope, probe, needle, surgical tool) | Stiffness | Depending on type of catheter dynamically being able to modulate the stiffness could allow non-traumatizing guidance within a vessel structure or organ. Probe guidance would have potentially same advantage from this. For endoscopes, needles and instruments a higher stiffness might be desirable to keep position stable (also in case of potential collisions with robotic arm internally or externally). Would work in combination with tactile feedback user interface. |
| Retraction or Stabilization (retractor, stabilizer) | Strength & Stiffness | For immobilizing of tissue (for example beating heart) the stiffness should be high to create a "resting" area on which the surgeon can perform suturing. A high strength of the arm will avoid that in case of collisions the immobilizing instrument will not be "knocked" off the immobilized are by external or internal sources. During normal operation (when instrument is not immobilizing) strength and stiffness are modulated to normal values. |
| Suturing (suturing tool, needle guide, pliers, stapler) | Strength | Avoidance of suture breakage, lower strength facilitates suturing task. |
| Ultrasound surface scanning (ultrasound probe) | Stiffness | Probe pressure for surface scan depending on tissue characteristics. Tissue characteristics can change within an organ based on status (cancer, myomas, etc.) and might require different pressure from scanning device to keep high quality image production stable. | fig.6

MEDICAL ROBOTIC SYSTEM WITH DYNAMICALLY ADJUSTABLE SLAVE MANIPULATOR CHARACTERISTICS

CROSS REFERENCE TO RELATED APPLICATIONS

This application is a continuation-in-part application of U.S. application Ser. No. 11/074,372 entitled "Grip Strength with Tactile Feedback for Robotic Surgery", filed Mar. 7, 2005, now U.S. Pat. No. 7,373,219, which is a continuation of U.S. application Ser. No. 10/437,771, filed May 13, 2003, now U.S. Pat. No. 6,879,880, which is a divisional application of U.S. application Ser. No. 09/544,153, filed Apr. 6, 2000, now U.S. Pat. No. 6,594,552, which claims priority from Provisional Application 60/128,157, filed Apr. 7, 1999, each of which is incorporated herein by reference.

FIELD OF THE INVENTION

The present invention generally relates to medical robotic systems and in particular, to a medical robotic system with dynamically adjustable slave manipulator characteristics.

BACKGROUND OF THE INVENTION

Medical robotic systems such as those used in performing minimally invasive surgical procedures offer many benefits over traditional open surgery techniques, including less pain, shorter hospital stays, quicker return to normal activities, minimal scarring, reduced recovery time, and less injury to tissue. Consequently, demand for minimally invasive surgery using such medical robotic systems is strong and growing.

Examples of medical robotic systems include the DA VINCI® Surgical System and the DA VINCI S® Surgical System from Intuitive Surgical, Inc., of Sunnyvale, Calif. Each of these systems includes a surgeon's console, a patient-side cart, a high performance three-dimensional ("3-D") vision system, and Intuitive Surgical's proprietary ENDOWRIST® articulating instruments, which are modeled after the human wrist so that when added to the motions of manipulators holding the surgical instruments, they allow at least six degrees of freedom of motion, which is comparable to or even greater than the natural motions of open surgery.

The DA VINCI® surgeon's console has a high-resolution stereoscopic video display with two progressive scan cathode ray tubes ("CRTs"). The system offers higher fidelity than polarization, shutter eyeglass, or other techniques. Each eye views a separate CRT presenting the left or right eye perspective, through an objective lens and a series of mirrors. The surgeon sits comfortably and looks into this display throughout surgery, making it an ideal place for the surgeon to display and manipulate 3-D intraoperative imagery.

The patient-side cart typically includes three or more robotic arm assemblies with corresponding slave manipulators for holding and manipulating medical devices such as surgical instruments and image capturing devices for performing and/or viewing a medical procedure at a surgical site within a patient. To manipulate these medical devices, the surgeon's console also includes input devices which may be selectively associated with the medical devices and their respective slave manipulators. Since the movements of the input devices and their associated medical devices are scaled, this allows the surgeon to perform intricate medical procedures with greater ease than conventional open surgery. Further, it may even allow the surgeon to perform medical procedures that are not even feasible using conventional open surgery techniques.

To perform a minimally invasive surgical procedure on a patient, one or more incisions are first made in the patient and cannulae inserted therein to gain access to a surgical site within the patient. Setup arms supporting the slave manipulators are then positioned so as to allow the slave manipulators to attach to respective of the cannulae. Surgical instruments engaged on the slave manipulators are then inserted into the cannulae and properly positioned and oriented in order to perform the procedure. A surgeon may then manipulate input devices which are coupled to the slave manipulators and their respective surgical instruments through one or more controllers to perform the surgical procedure.

The slave manipulators generally have fixed strength and stiffness characteristics. The strength of each slave manipulator is a function of the maximum motor torque commanded by its joint controllers to drive its joints, the efficiency of any drive trains used in effecting its movement, and the total friction in its joints. The stiffness (around a desired setpoint) of each slave manipulator is a function of the feedback control law and control parameters used in its joint controllers.

In certain applications, however, the fixed values for the slave manipulator's strength and stiffness may be too low or too high. For example, when the slave manipulator is holding and manipulating a heart stabilizer, if the slave manipulator's strength is too low, this may result in a potential safety hazard while the stabilizer is being applied against a patient's heart if an external collision with the slave manipulator's robotic arm results in displacing the heart more than it is safe to do so. On the other hand, if the slave manipulator's strength is too high, then too much force might be inadvertently applied on the external or internal patient anatomy, thus also causing an unsafe condition. Further, a slave manipulator having high stiffness and strength may be difficult for support staff to manually position during setup or performance of a medical procedure.

OBJECTS AND SUMMARY OF THE INVENTION

Accordingly, one object of one or more aspects of the present invention is a method for dynamically adjusting a characteristic of a slave manipulator to improve surgeon performance of a medical procedure.

Another object of one or more aspects of the present invention is a method for dynamically adjusting a characteristic of a slave manipulator to improve system safety.

Another object of one or more aspects of the present invention is a method for dynamically adjusting a characteristic of a slave manipulator according to one or more criteria such as a current mode of operation of the slave manipulator, a functional type of medical device currently being held and manipulated by the slave manipulator, and a current phase of a medical procedure being performed using the slave manipulator.

Another object of one or more aspects of the present invention is a method for dynamically adjusting a characteristic of a slave manipulator that warns the surgery staff when excessive forces are being generated and/or prevents the user from switching to system modes of operation that could be hazardous in the presence of such excessive forces.

Still another object of one or more aspects of the present invention is a medical robotic system configured with one or more of such methods for dynamically adjusting a characteristic of a slave manipulator.

These and additional objects are accomplished by the various aspects of the present invention, wherein briefly stated, one aspect is a method for dynamically adjusting a characteristic of a slave manipulator adapted to manipulate a medical device according to operator manipulation of an input device during a medical procedure performed on a patient, comprising: determining whether the characteristic of the slave manipulator is to be adjusted by using criteria including a functional type of the medical device and a current phase of the medical procedure; determining whether a change in a parameter of the control system that results in adjusting the characteristic would also result in an actuator command generated with a control system to drive an actuator of the slave manipulator that exceeds a threshold value immediately following the change in the parameter; and changing the characteristic if it is determined that the characteristic is to be adjusted and if it is determined that the actuator command would not exceed the threshold value immediately following change of the parameter.

Another aspect is a method for dynamically adjusting a characteristic of a slave manipulator adapted to manipulate a medical device according to operator manipulation of an input device as controlled by a control system during a medical procedure performed on a patient, comprising: determining whether a change in a parameter of the control system that results in adjusting the characteristic would also result in an actuator command generated within the control system to drive an actuator of the slave manipulator that exceeds a threshold value immediately following the change in the parameter; and changing the parameter so as to adjust the characteristic if it is determined that the characteristic is to be adjusted and the actuator command would not exceed the threshold value immediately following the change in the parameter.

Additional objects, features and advantages of the various aspects of the present invention will become apparent from the following description of its preferred embodiment, which description should be taken in conjunction with the accompanying drawings.

BRIEF DESCRIPTION OF THE DRAWINGS

FIG. 6 illustrates a table of criteria and adjustable characteristics that are to be adjusted by a method for dynamically adjusting an adjustable characteristic of a slave manipulator utilizing aspects of the present invention.

DETAILED DESCRIPTION OF THE PREFERRED EMBODIMENT

Figure 1:
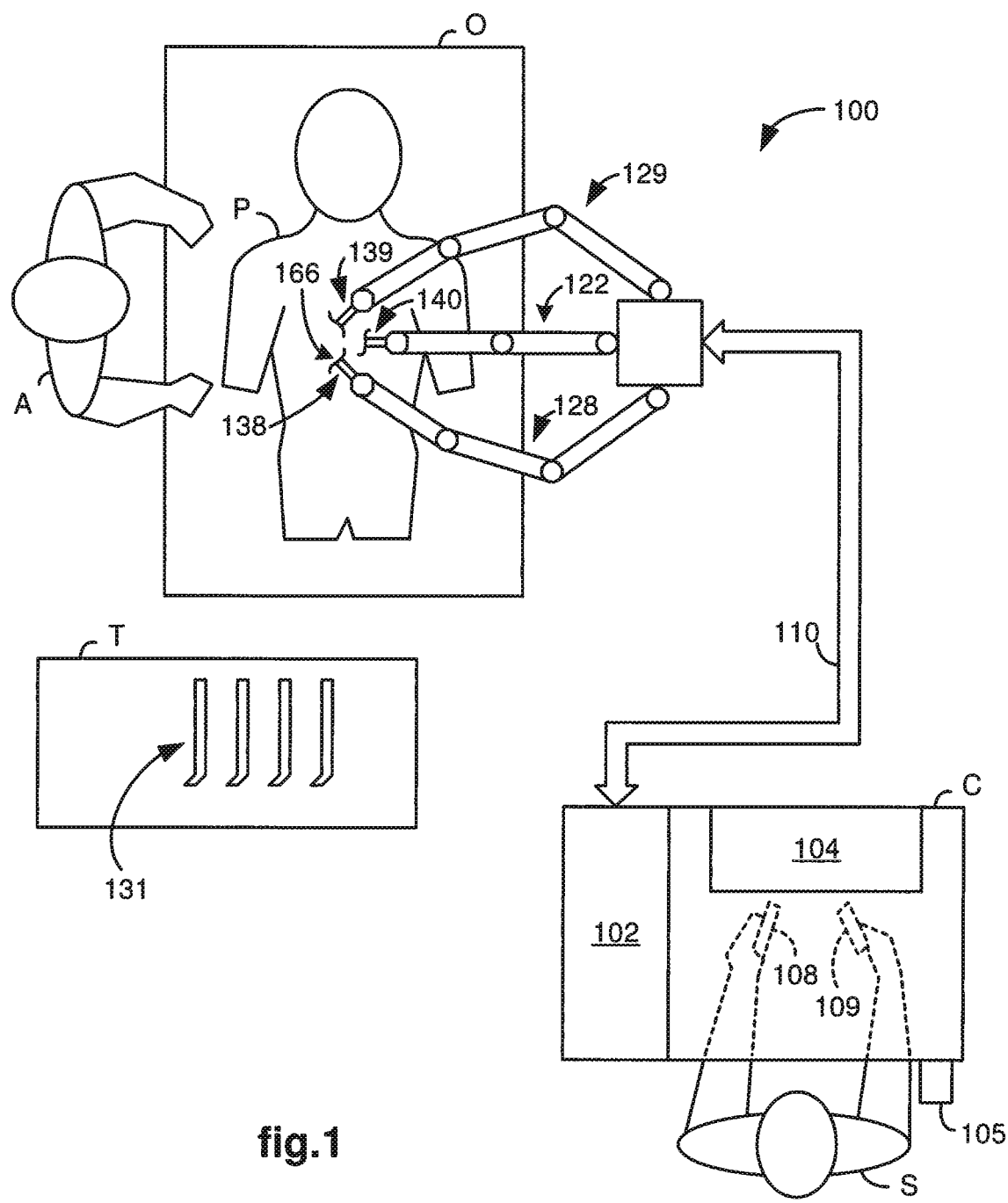
FIG. 1 illustrates a top view of an operating room employing a medical robotic system utilizing aspects of the present invention.

FIG. 1 illustrates, as an example, a top view of an operating room employing a medical robotic system. The medical robotic system in this case is a minimally invasive robotic surgical system 100 including a Console ("C") utilized by a Surgeon ("S") while performing a medical procedure, such as a diagnostic or surgical procedure, with assistance from one or more Assistants ("A"), on a Patient ("P") who is reclining on an Operating table ("0").

The Console includes a 3-D monitor 104 for displaying a 3-D image of a surgical site to the Surgeon, left and right manipulatable input devices 108, 109, a foot pedal 105, and a processor 102. The input devices 108, 109 may include any one or more of a variety of input devices such as joysticks, gloves, trigger-guns, hand-operated controllers, or the like. The processor 102 may be a dedicated computer integrated into the Console or positioned next or near to it, or it may be broken up into a number of processing or controller components that are distributed in a distributed processing fashion throughout the system 100.

The Surgeon performs a medical procedure by manipulating the input devices 108, 109 (also referred to herein as "master manipulators") so that the processor 102 causes slave manipulators of their respectively associated robotic arm assemblies 128, 129 to manipulate their respective removably coupled surgical instruments 138, 139 (also referred to herein as "tools") accordingly, while the Surgeon views the surgical site in 3-D on the Console monitor 104 as it is captured by a stereoscopic endoscope 140.

Each of the tools 138, 139, as well as the Endoscope 140, is conventionally inserted through a tool guide (not shown) into the Patient so as to extend down to the surgical site through a corresponding minimally invasive incision such as Incision 166. The number of surgical tools used at one time and consequently, the number of robotic arms being used in the system 100 will generally depend on the medical procedure being performed and the space constraints within the operating room, among other factors. If it is necessary to change a tool being used during a procedure, the Assistant may remove the tool no longer being used from its robotic arm assembly, and replace it with another tool 131 from a Tray ("T") in the operating room.

Each of the robotic arm assemblies 122, 128, 129 includes a slave manipulator and setup arms. The slave manipulators are robotically moved using motor controlled joints (also referred to herein as "active joints") in order to manipulate and/or move their respectively held medical devices. The setup arms may be manually manipulated by releasing normally braked joints (also referred to herein as "setup joints") to horizontally and vertically position the robotic arm assemblies 122, 128, 129 so that their respective medical devices may be inserted into their respective tool guides.

Preferably, the monitor 104 is positioned near the Surgeon's hands so that it will display a projected image that is oriented so that the Surgeon feels that he or she is actually looking directly down onto the operating site. To that end, images of the tools 138, 139 preferably appear to be located substantially where the Surgeon's hands are located.

The processor 102 performs various functions in the system 100. One important function that it performs is to translate and transfer the mechanical motion of input devices 108, 109 to their respective slave manipulators of robotic arm assemblies 128, 129 through control signals over bus 110 so that the Surgeon can effectively manipulate their respective tools 138, 139. Another important function is to implement various control system processes and the methods as described herein.

Although described as a processor, it is to be appreciated that the processor 102 may be implemented in practice by any combination of hardware, software and firmware. Also, its functions as described herein may be performed by one unit, or divided up among different components, each of which may be implemented in turn by any combination of hardware, software and firmware.

For additional details on the construction and operation of medical robotic systems such as described herein, see, e.g., commonly owned U.S. Pat. No. 6,493,608 "Aspects of a Control System of a Minimally Invasive Surgical Apparatus," and commonly owned U.S. Pat. No. 6,424,885 "Camera Referenced Control in a Minimally Invasive Surgical Apparatus," which are incorporated herein by reference.

Figure 2:
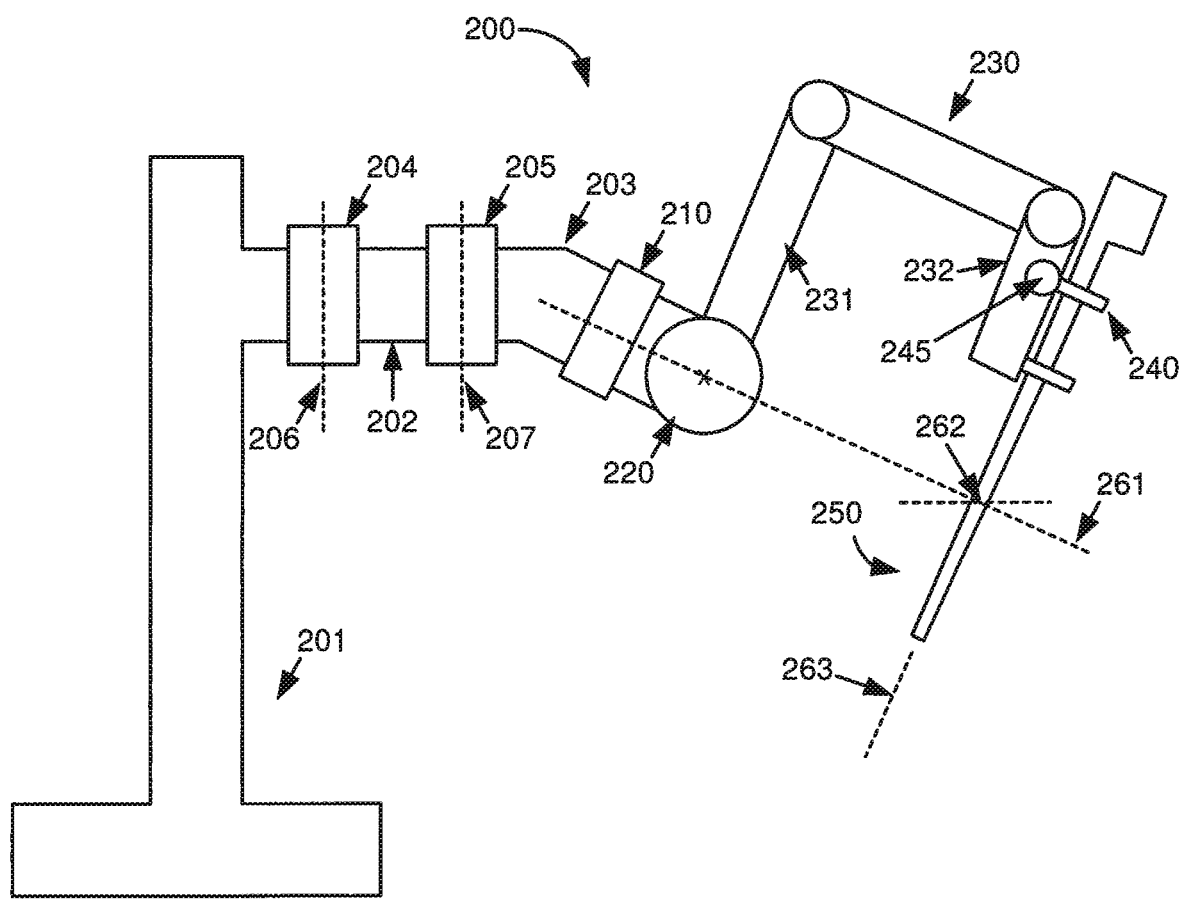
FIG. 2 illustrates a simplified side view of a robotic arm assembly that is usable with various aspects of the present invention.

FIG. 2 illustrates, as an example, a side view of a simplified (not necessarily in proportion or complete) robotic arm assembly 200 (which is representative of the robotic arm assemblies 128, 129) holding a surgical instrument 250 (which is representative of tools 138, 139) for performing a medical procedure. The surgical instrument 250 is removably held in tool holder 240. The robotic arm assembly 200 is mechanically supported by a base 201, which may be part of a patient-side movable cart or affixed to the operating table or ceiling. It includes links 202, 203 which are coupled together and to the base 201 through horizontal setup joints 204, 205.

The setup joints 204, 205 in this example are passive joints that allow manual positioning of the arm 200 when their brakes are released. For example, setup joint 204 allows link 202 to be manually rotated about axis 206, and setup joint 205 allows link 203 to be manually rotated about axis 207. The setup arm or portion of the robotic arm assembly 200 includes these setup joints.

Although only two links and two setup joints are shown in this example, more or less of each may be used as appropriate in this and other robotic arm assemblies in conjunction with the present invention. For example, although setup joints 204, 205 are useful for horizontal positioning of the arm 200, additional setup joints may be included and useful for limited vertical and angular positioning of the arm 200. For major vertical positioning of the arm 200, however, the arm 200 may also be slidably moved along the vertical axis of the base 201 and locked in position.

The robotic arm assembly 200 also includes three active joints driven by motors (or more generally, actuators). A yaw joint 210 allows arm section 230 to rotate around an axis 261, and a pitch joint 220 allows arm section 230 to rotate about an axis perpendicular to that of axis 261 and orthogonal to the plane of the drawing. The slave manipulator of the robotic arm assembly 200 includes these active joints.

The arm section 230 is configured so that sections 231, 232 are always parallel to each other as the pitch joint 220 is rotated by its motor. As a consequence, the instrument 250 may be controllably moved by driving the yaw and pitch motors so as to pivot about the pivot point 262, which is generally located through manual positioning of the setup joints 204, 205 so as to be at the point of incision into the patient. In addition, an insertion gear 245 may be coupled to a linear drive mechanism (not shown) to extend or retract the instrument 250 along its axis 263.

Although each of the yaw, pitch, and insertion joints or gears, 210, 220, 245, is controlled by an individual joint or gear controller, the three controllers are controlled by a common master/slave control system so that the slave manipulator of the robotic arm assembly 200 may be controlled through user (e.g., surgeon) manipulation of its associated master manipulator.

Figure 3:
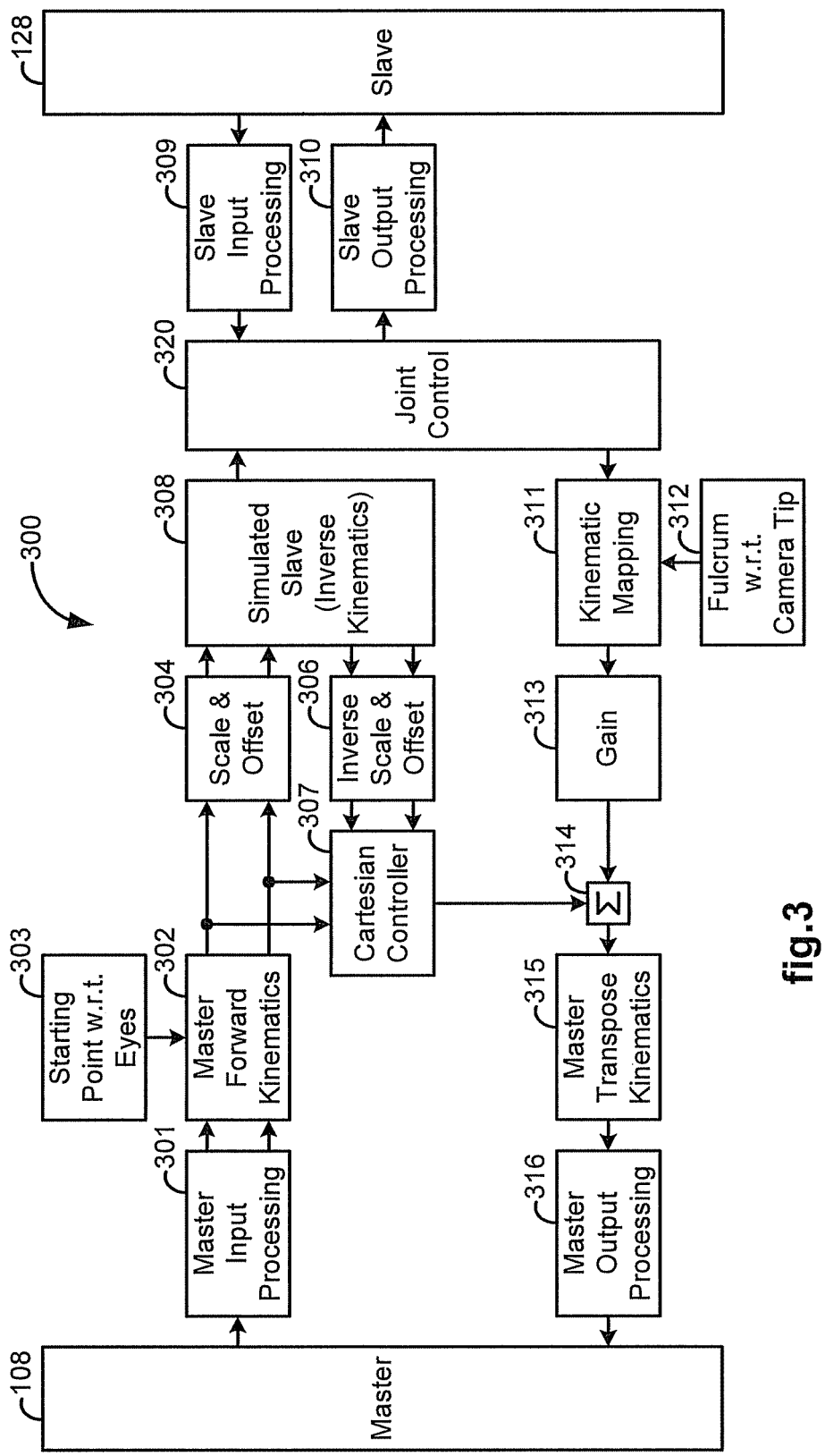
FIG. 3 illustrates a block diagram of a master/slave control system utilizing aspects of the present invention.

FIG. 3 illustrates, as an example, a block diagram of a master/slave control system 300 for controlling movement of the slave manipulator of the robotic arm assembly 128 and consequently, the position and orientation of its attached tool 138, as commanded by movement of the master manipulator 108 by a surgeon. A similar control system may also be provided for the slave manipulator of the robotic arm assembly 129 and its associated master manipulator 109.

Both the master and slave manipulators include a number of linkages connected by joints so as to facilitate multiple degrees-of-freedom movement. As the surgeon moves the master manipulator 108 from one position to another during the course of performing a surgical procedure, sensors associated with the master manipulator joints provide information indicating such command movement in master joint space, and sensors associated with the slave manipulator joints provide information indicating slave manipulator and consequently, tool 138 movement in slave joint space for feedback purposes. In order to better detect and control fine movements of their respective joints (e.g., in the target velocity range of 0.0005 to 0.01 radians per second at the joint, including the motion during the transition from zero velocity to the velocity in the target range), high resolution encoders are preferably used for the joint sensors.

A master input processing unit 301 receives the information of the master joint positions, which are sampled at the control system processing rate (e.g., 1300 Hz in the present example), from the master joint sensors in the master manipulator 108, and computes joint velocities from the sensed joint positions. A master forward kinematics processing unit 302 receives the master joint positions and velocities from the master input processing unit 301, transforms them from master joint space to corresponding positions and velocities of the master frame (i.e., the frame associated with the master manipulator 108) in Cartesian space relative to the eye reference frame (i.e., the reference frame associated with the position of the surgeon's eyes), using, for example, a Jacobian matrix and eye related information separately determined and provided in block 303.

A scale and offset processing unit 304 receives the Cartesian position and velocity commands from the master forward kinematics processing unit 302, scales the commanded movement according to a scale factor selected to perform the surgical procedure, and takes into account offsets to generate desired slave tool frame (i.e., the frame associated with the tool 138) positions and velocities. The scale adjustment is useful where small movements of the slave manipulator of the robotic arm assembly 128 are desired relative to larger movement of the master manipulator 108 in order to allow more precise movement of the slave tool 138 at the surgical site. The offsets, on the other hand, determine, for example, the corresponding position and/or orientation of an end effector frame (e.g., the frame associated with an end effector of the tool 138) in the camera reference frame (i.e., the frame associated with the distal tip of the endoscope 140) relative to a position and orientation of the master frame in the eye reference frame.

A simulated slave processing unit 308 receives desired slave tool frame position and velocity commands from the scale and offset processing unit 304, and limits the desired slave tool frame position, orientation and velocities, to assigned Cartesian Limits for instance to enforce correct and intuitive operation of the tool 138 by keeping it within its dexterous workspace. The simulated slave processing unit 308 generates simulated slave joint positions and velocities corresponding to the limited slave tool frame positions and velocities, while making sure that the generated slave joint positions and velocities do not exceed the actual slave joint's range of motion and maximum velocities (i.e., joint limits) even in the vicinity of kinematic singularities for the slave kinematics.

An inverse scale and offset processing unit 306 receives the simulated joint position and velocity commands from the simulated slave processing unit 308, and performs an inverse function to that of the scale and offset processing unit 304 on them. A Cartesian controller 307 receives as first inputs, the inputs to the scale and offset processing unit 304 and as second inputs, the outputs of the inverse scale and offset processing unit 306. The Cartesian controller 307 then generates an error signal as a difference of the first and second inputs, and a Cartesian force "$F_{CART}$" from the error signal such as with the following formula:

$$F_{CART}=K(\Delta x)+B(\Delta \dot{x})$$

where "K" is a spring constant, "B" is a damping constant, "$\Delta \dot{x}$" is the difference between the Cartesian velocity inputs to the Cartesian controller 307 and "$\Delta x$" is the difference between the Cartesian position inputs to the Cartesian controller 307. For an orientation error, a corresponding torque in Cartesian space is determined.

A master transpose kinematics processing unit 315 receives the Cartesian force $F_{CART}$ through a summation node 314, and generates a corresponding torque in joint space using, for example, the Jacobian transpose matrix and kinematic relationships associated with the master manipulator 108. A master output processing unit 316 receives the master torque signals from the master transpose kinematics processing unit 315, generates electrical currents corresponding to the master torque signals, and supplies the electrical currents to corresponding master joint motors of the master manipulator 108. As a result, a surgeon operating the master manipulator 108 feels the Cartesian force, $F_{CART}$, whenever the surgeon is commanding a position or velocity which exceeds system Cartesian or slave joint limits, or would result in a kinematic singularity condition for the slave manipulator of the robotic arm assembly 128.

As the master input processing unit 301 is receiving master joint positions from sensors in the master manipulator 108, a slave input processing unit 309 is also receiving slave joint positions from position sensors in the slave manipulator at the control system processing rate. A joint control unit 320 receives the slave joint positions from the slave input processing unit 309 and the simulated joint position commands provided from the simulated slave processing unit 308, and generates slave torque command signals for the slave joint motors and master torque feedback command signals for the master joint motors.

The slave torque command signals are generated by the joint control unit 320 so as to drive joints of the slave manipulator until feedback errors calculated in the joint control unit 320 zero out. A slave output processing unit 310 receives the slave torque command signals from the joint control unit 320, converts them into appropriate electrical currents, and supplies the electrical currents to the joint motors of the slave manipulator so as to drive the motors accordingly.

The master torque feedback command signals are generated by the joint control unit 320 as a function of the slave joint position and velocity tracking errors so as to reflect forces being exerted against the tool 138 or its slave manipulator back to the master manipulator 108 so that they may be felt by the surgeon. A kinematic mapping unit 311 receives the master torque feedback command signals from the joint control unit 320, and generates the corresponding Cartesian force at the tip of the tool 138 relative to the camera frame of the endoscope 140 using the slave kinematic configuration and the previously calculated slave fulcrum (e.g., pivot point) position information provided in block 312.

A gain 313 adjusts the magnitude of the Cartesian force so as to ensure system stability while providing adequate force sensation to the surgeon. The gain adjusted Cartesian force is then passed through the summation node 314, and processed along with the Cartesian force provided by the Cartesian controller 307 through the Master transpose kinematics processing unit 315 and Master output processing 316 as previously described in reference to their processing of the Cartesian force provided by the Cartesian controller 307.

Additional details related to conventional aspects of the master/slave control system 300, such as the various reference frames referred to herein and the calculation of the surgeon eye related information provided in block 303 and the slave fulcrum information provided in block 312, which are based upon well-known mathematics, are described, for example, in previously incorporated by reference and commonly owned U.S. Pat. No. 6,424,885, "Camera Referenced Control in a Minimally Invasive Surgical Apparatus."

The joint control unit 320 includes a joint controller for each active joint and gear of the slave manipulator of the robotic arm assembly 128 that is being controlled by the master/slave control system 300. In particular, where the slave manipulator 128 includes a yaw joint 210, a pitch joint 220, and an insertion axis gear 245, such as the robotic arm assembly 200 of FIG. 2, each of these joints or gears will have its own controller. To simplify the description herein and in the claims, the term "joint" is to be understood as a connection (translational or revolute) between two links, and may include gears as well as any other controllable component coupled to linear drive mechanisms that may be used in controlling robotic arm assemblies.

Figure 4:
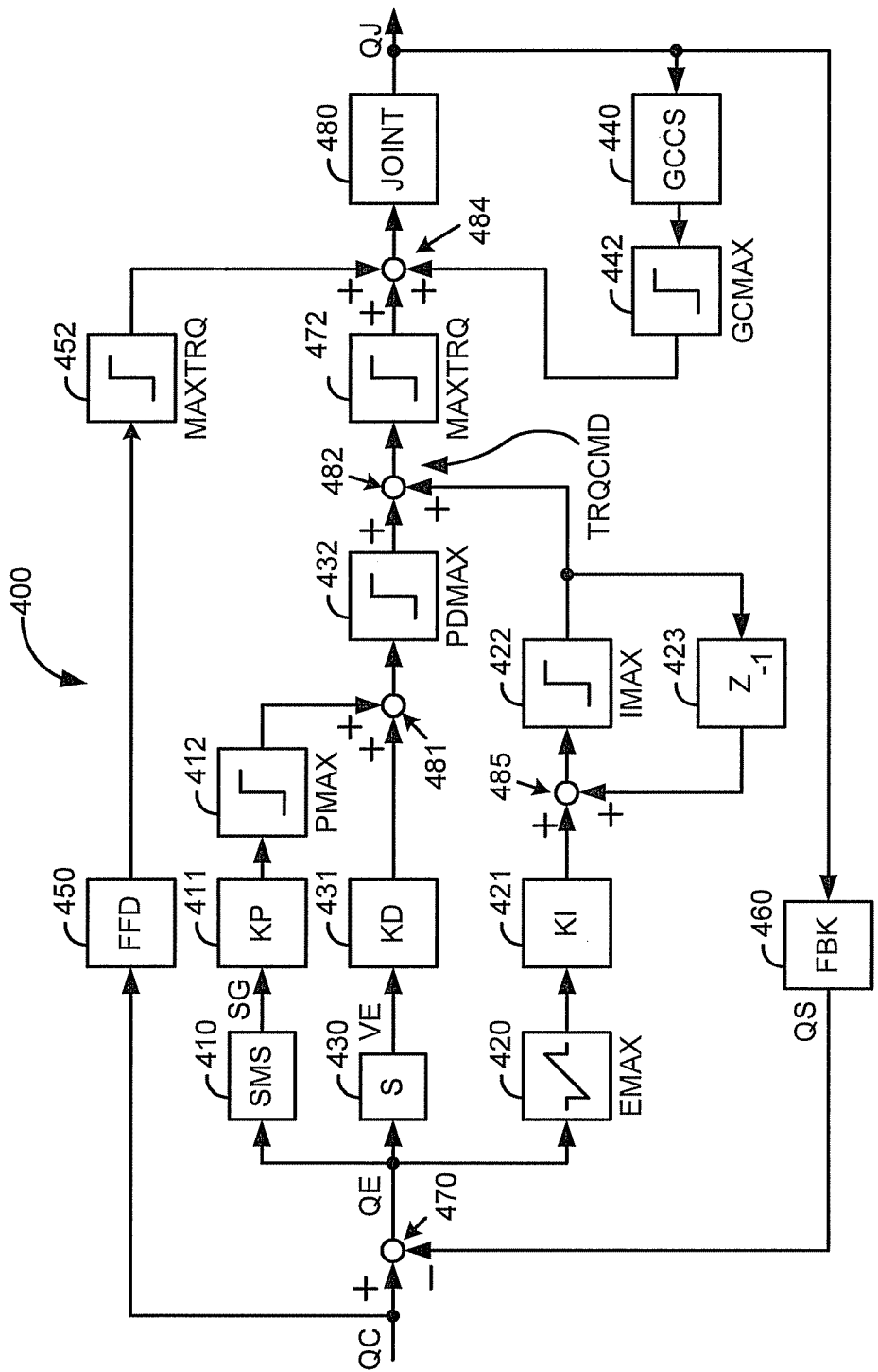
FIG. 4 illustrates a block diagram of a joint controller with gravity compensation, utilizing aspects of the present invention.

FIG. 4 illustrates, as an example, a block diagram of a joint controller 400 with gravity compensation, which is included in the joint control unit 320 of the master/slave control system 300. In this example, only the position command QC and feedback QS are shown to simply the description. The velocity VC and acceleration AC commands are not shown or used in this simplified example, but their use is contemplated for a more sophisticated controller, such as described in commonly owned U.S. Pat. No. 7,689,320, "Robotic Surgical System with Joint Motion Controller Adapted to Reduce Instrument Tip Vibrations," filed Aug. 24, 2006, which is incorporated herein by reference.

A feedforward path (also referred to herein as a "feedforward controller") extends from the QC command to node 484 including blocks 450 and 452. Block 450 preferably includes logic for reducing internally generated frictional and inertial resistance when manually moving the slave manipulator, such as described in commonly owned U.S. Pat. No. 7,819,859, "Control System for Reducing Internally Generated Frictional and Inertial Resistance to Manual Positioning of a Surgical Manipulator," filed Jun. 30, 2006, which is incorporated herein by reference. Block 452 is a torque limiting function that limits the torque command from the feedforward path to a maximum torque value MAXTRQ.

A feedback path (also referred to herein as a "feedback controller") includes sliding surface, integral, and derivative paths extending from node 470 to node 482. The sliding surface path includes block 410, which is preferably a Sliding Surface (SS) function such as used in sliding mode control applications, block 411, which is a gain KP, and block 412, which is a limiter that limits the output of the sliding surface path to a torque value of PMAX. The integral path includes block 420, which is an input limiter that limits the magnitude of the position error that is to be processed through the path; block 421, which is an integrator gain KI; block 422, which is a limiter that limits the output of the integrator path to a torque value of IMAX; and block 423, which stores the prior output $Z_{-1}$ of the integrator path which is to be summed with the output of 421 at node 485 to perform the digital integrator function. The derivative path includes block 430, which is a derivative function (indicated by the Laplace transform "S") that generates a derivative of the position error QE to generate a velocity error VE, and block 431, which is a derivative path gain KD.

Additional details on such a sliding mode control may be found in commonly owned U.S. Pat. No. 7,741,802, "Medical Robotic System with Programmably Controlled Constraints on Error Dynamics," filed Dec. 20, 2006, which is incorporated herein by this reference.

The outputs of the sliding surface and derivative paths are added at node 481. Block 432 is a limiter that limits the value passed from node 481 to node 482 to a torque value of PDMAX. The outputs of block 432 and the integral path are added at node 482 to generate the torque command TRQCMD. Block 472 is another limiter that limits the value passed from node 482 to node 484 to a maximum torque value MAXTRQ.

Block 460 is a sensor feedback gain FBK which nominally has a value of one in the present example. A gravity compensation control system ("GCCS") 440 receives information of sensed joint positions for all active joints of the slave manipulator 128, including the position QJ of the joint 480, and generates appropriate torque commands for their respective motors to compensate for any gravity imbalance that may occur during movement of the slave manipulator 128. Details of one such a gravity compensation control system are provided in previously incorporated by reference and commonly owned, U.S. Pat. No. 7,819,859. Other known gravity compensation control systems may also be used. Block 442 receives the output of the gravity compensation control system 440 and limits it to a torque value of GCMAX.

A summing node 484 receives the outputs of limiter 452 (from the feedforward path), limiter 472 (from the feedback path), and limiter 442 (from the gravity compensation control system 440). Torque budgeting is preferably employed so that the maximum commmandable torque value MAXTRQ is budgeted between the integrator path torque command, which is limited to IMAX, and the combined sliding surface and derivative path torque command, which is limited to PDMAX. An extra torque margin is provided (i.e., the actual commandable torque limit of the joint motor is greater than the sum of the maximum commandable torque value MAXTRQ and the maximum allowable gravity compensation value GCMAX) to accommodate feedforward path and control transients.

Up to this point in the description, a fixed parameter master/slave control system 300 for the robotic arm assembly 128 has been described. With the gains and limits of the joint controller 400 fixed, however, its corresponding slave manipulator has a fixed strength and stiffness. In order to adjust characteristics of the slave manipulator, parameter changes in the control system 300, and in particular, in its joint controllers, such as joint controller 400, may be performed. Since these characteristics of the slave manipulator are adjustable, they are referred to as being "adjustable characteristics" of the slave manipulator.

Figure 5:
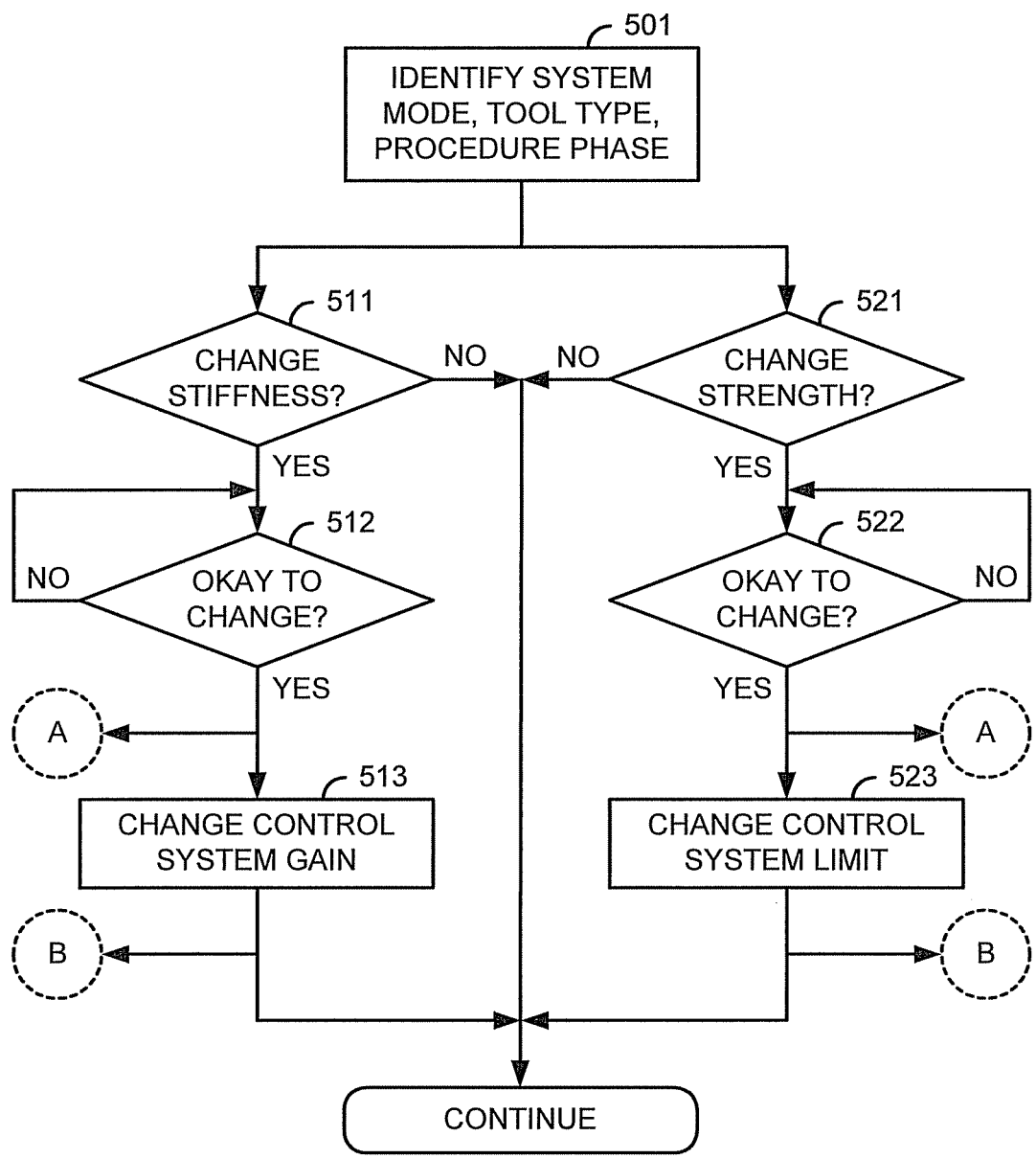
FIG. 5 illustrates a flow diagram of a method for dynamically adjusting an adjustable characteristic of a slave manipulator, utilizing aspects of the present invention.

FIG. 5 illustrates, as an example, a flow diagram of a method, preferably performed by the processor 102 in the medical robotic system 100, for dynamically adjusting an adjustable characteristic of a slave manipulator (such as the slave manipulators of the robotic arm assemblies 122, 128, 129).

In 501, the method first identifies certain criteria that will be used in determining whether one or more adjustable characteristics of the slave manipulator are to be adjusted from their normal or unadjusted values. Examples of such criteria include: the current mode of operation of the slave manipulator (e.g., arm locked in place with or without a medical device, or arm in normal operation so as to respond to operator manipulation of an associated input device), the functional type of the medical device currently being held and manipulated by the slave manipulator (e.g., a heart-stabilizer with suction, a needle driver for suturing tissue together, or a tissue retractor for retracting and holding in place retracted tissue), and the current phase of the medical procedure being performed on a patient using the medical device held by the slave manipulator (e.g., positioning a heart-stabilizer instrument versus having it locked in place while applying suction so that it is firmly attached to the heart, or positioning a retractor instrument versus having it locked in place exposing organs, specific anatomy, and tissue planes without motion).

In 511, the method determines whether a first adjustable characteristic of the slave manipulator (e.g., its stiffness) is to be adjusted according to the criteria identified in 501. In 521, the method also determines whether a second adjustable characteristic of the slave manipulator (e.g., its strength) is to be adjusted according to the criteria identified in 501. Although not shown, other adjustable characteristics of the slave manipulator may be defined, and the method may also determine whether those other adjustable characteristics are to be adjusted according to the criteria identified in 501. For example, other adjustable characteristics of the slave manipulator may include the instrument tip Cartesian stiffness or strength, i.e. the stiffness in the x, y, and z directions defined with respect to the tip and the rotational stiffness along the same directions, and the maximum force applicable in the same x, y, and z directions (as opposed to the strength and stiffness of the individual joints of the patient side slave manipulator as described above).

In order to make the determinations in 511 and 521, a set of expert rules is defined and stored in a memory (such as a hard disk) so as to be made available to the processor 102, which is executing a computer program embodying the method. As an example, FIG. 6 illustrates a table containing information from which a set of expert rules may be derived. Referring to the table, several different phases of medical procedures are shown with representative medical devices identified that may be used in performing those phases of the medical procedures. Also shown are adjustable characteristics (e.g., stiffness and strength) that are to be considered for adjustment during the phases, and comments from which determinations may be made of whether the adjustable characteristics should be strengthened or weakened. The specific numerical amount of strengthening or weakening is to be determined empirically by medical experts on an instrument by instrument basis during the system design and is also saved in a memory available to processor 102.

For example, for "mechanical" surgical cutting devices (e.g., a saw), a high stiffness would be desirable to avoid "kickback" off an anatomic structure (e.g., tissue, vessel, organ, bone, etc.) being cut. However, for medical devices incorporating a vacuum suction, a lower stiffness may be advantageous so that the suction of the medical device may conform to a tissue or organ structure or surface. Thus, the stiffness of the slave manipulator may be adjusted up or down depending upon the level of stiffness for the unadjusted characteristic, the current phase of a medical procedure being performed, and the medical device being used to perform the current phase of the medical procedure.

If the determination in 511 is NO, then the method continues and makes no adjustment to the slave manipulator stiffness characteristic at this time. On the other hand, if the determination in 511 is YES, then in 512, the method next determines whether it is permissible to adjust the adjustable stiffness characteristic at the time. Likewise, if the determination in 521 is NO, then the method continues and makes no adjustment to the slave manipulator strength characteristic at this time. On the other hand, if the determination in 521 is YES, then in 522, the method next determines whether it is permissible to adjust the adjustable strength characteristic at the time. Details for exemplary processes for 512 and 522 are discussed below.

If the determination in 512 is NO, then the method loops back to periodically check if it is permissible at that time to make the stiffness adjustment. Once the determination in 512 is YES, then in 513, the method makes the stiffness adjustment by, for example, adjusting at least the sliding surface gain KP of the joint controller 400. Increasing the gain KP in this case results in increasing the stiffness of the slave manipulator, because feedback errors are magnified. Conversely, reducing the gain KP results in reducing the stiffness of the slave manipulator. To ensure proper dynamic response and stability of the control system, however, appropriate gain changes may also be made to the derivative and integrator path gains KD and KI as well. Such gain value determinations may be made computationally using conventional control theory techniques or empirically through simulations of the medical robotic system 100 for various phases of medical procedures using various medical devices.

In a similar manner, if the determination in 522 is NO, then the method loops back to periodically check if it is permissible at that time to make the strength adjustment. Once the determination in 522 is YES, then in 523, the method makes the strength adjustment by, for example, adjusting the maximum commandable torque MAXTRQ by changing the limit MAXTRQ of the limiter 472 of the joint controller 400. Thus, more or less commandable torque MAXTRQ is available to the joint controller 400 to overcome feedback errors resulting in external forces being applied to the slave manipulator (i.e., forces not generated through operation of the master/slave control system 300). Increasing the limit MAXTRQ in this case results in increasing the strength of the slave manipulator, because larger feedback torque commands may be provided to the joint motor. Conversely, reducing the limit MAXTRQ results in reducing the strength of the slave manipulator.

Although changing the parameter(s) for only one joint controller is described herein, it is to be appreciated that in practice, all or less than all of the joint controllers of master/slave control system 300 may have parameters changed as described herein for the joint controller 400. Further, values for the changed parameters may be different for the different joint controllers so as to fine tune the stiffness and strength adjustments to the slave manipulator.

Indicators or flags may be set following YES determinations in 512 and 522 in order to notify surgery staff that characteristics of the slave manipulator are to be adjusted, or after execution of 513 and 523 to notify surgery staff that the characteristics have been adjusted. Alternatively, or in addition, these indicators or flags may be used to trigger other processes such as initiating monitoring for excessive forces and warning the surgery staff when they occur.

Figure 7:
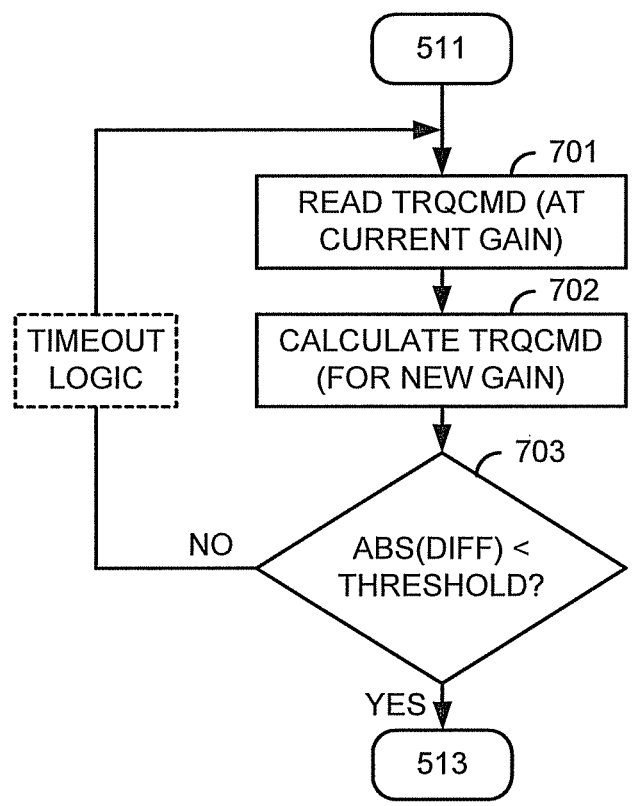
FIG. 7 illustrates a flow diagram of a method for determining whether it is permissible to change a control system parameter for adjusting the stiffness of a slave manipulator, utilizing aspects of the present invention.
Figure 8:
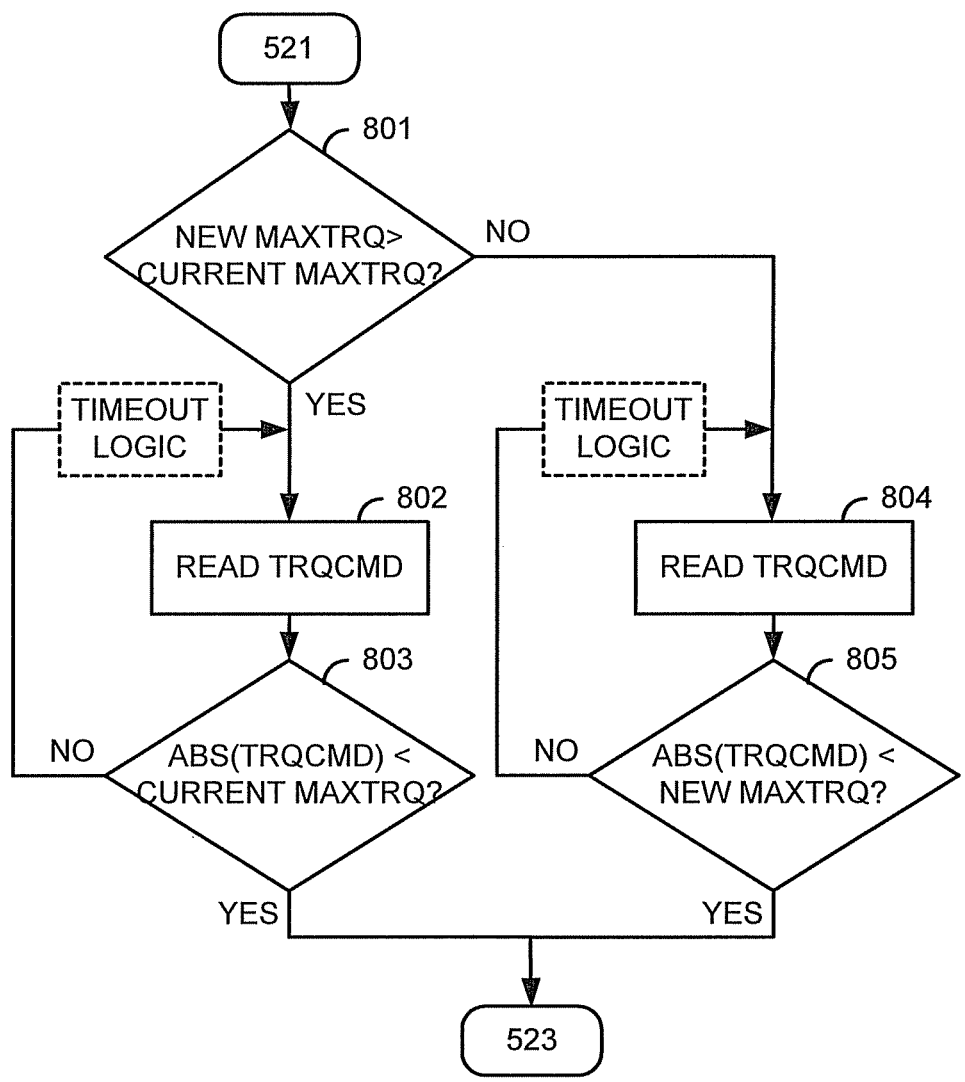
FIG. 8 illustrates a flow diagram of a method for determining whether it is permissible to change a control system parameter for adjusting the strength of a slave manipulator, utilizing aspects of the present invention.

FIG. 7 illustrates, as an example, a flow diagram of a method for performing 512 of FIG. 5 to determine whether it is permissible to change a control system gain for adjusting the stiffness of a slave manipulator. Similarly, FIG. 8 illustrates, as an example, a flow diagram of a method for performing 522 of FIG. 5 to determine whether it is permissible to change a control system limit for adjusting the strength of a slave manipulator. One consideration in making the determinations in 512 and 522 is to try to avoid making jerks or discontinuities in the joint motor torques when making the control system parameter changes. Another consideration is to avoid even a slow movement of the instrument in the patient's body unless the surgeon's input has changed. For instance, a stiffness adjustment while the surgical instrument or the manipulator holding it is pressed against an external compliant object or anatomy, can produce such an undesired slow change in the instrument position without any input from the surgeon. Accordingly, the threshold values used and described herein are selected with such and possibly other considerations in mind.

Referring first to FIG. 7, in 701, the current torque command TRQCMD generated by adding the sliding surface, derivative, and integral path outputs using their current gains in the joint controller 400 is read out or otherwise obtained from the control system processing calculations performed by the processor 102. In 702, a prospective torque command TRQCMD is generated (for the same instant in time as the current torque command TRQCMD) by adding proportional, derivative, and integral path outputs calculated using new gains in those paths according to the stiffness adjustment determined in 511 of FIG. 5.

In 703, the absolute value of a difference between the current torque command TRQCMD and the prospective torque command TRQCMD is then compared against a threshold value. If the absolute value of the difference is less than the threshold value, then the determination in 703 is a YES, and the gain changes to the joint controller 400 may be made at that time to adjust the stiffness characteristic. On the other hand, if the absolute value of the difference is greater than the threshold value, then the determination in 703 is a NO, and the gain changes to the joint controller 400 may not be made at that time to adjust the stiffness characteristic. In this latter case, the method loops through 701-703 until it is determined in 703 that the gain changes to the joint controller 400 may be made. Optional timeout logic may be inserted in the loop 701-703 to notify surgery staff, or to take other appropriate action, in the event that the gain changes to the joint controller 400 may not be made within a reasonable period of time.

Referring now to FIG. 8, in 801, a determination is made whether the new maximum torque limit MAXTRQ (which is in accordance with the determination made in 521 of FIG. 5) is greater than the current maximum torque limit MAXTRQ. If the determination in 801 is YES, then processing of the method continues with 802. On the other hand, if the determination in 801 is NO, then processing of the method continues with 804.

In 802, the current torque command TRQCMD is read out or otherwise obtained from the control system processing calculations performed by the processor 102. In 803, a determination is made whether the absolute value of the current torque command TRQCMD is less than the current maximum torque MAXTRQ (i.e., the limiter 472 is not currently saturated using the current maximum torque limit MAXTRQ). If the determination in 803 is YES, then the maximum torque limit change to the limiter 472 may be made at that time to adjust the strength characteristic of the slave manipulator. On the other hand, if the determination in 803 is NO, then the maximum torque limit change to the limiter 472 may not be made at that time, and the method loops through 802-803 until the determination in 803 results in a YES. Optional timeout logic may be inserted in the loop 802-803 to notify surgery staff, or to take other appropriate action, in the event that the limit changes to the joint controller 400 may not be made within a reasonable period of time.

In a similar fashion, in 804, the current torque command TRQCMD is read out or otherwise obtained from the control system processing calculations performed by the processor 102. In 805, a determination is made whether the absolute value of the current torque command TRQCMD is less than the new maximum torque MAXTRQ (i.e., the limiter 472 will not be saturated using the new maximum torque limit MAXTRQ). If the determination in 805 is YES, then the maximum torque limit change to the limiter 472 may be made at that time to adjust the strength characteristic of the slave manipulator. On the other hand, if the determination in 805 is NO, then the maximum torque limit change to the limiter 472 may not be made at that time, and the method loops through 804-805 until the determination in 805 results in a YES. Optional timeout logic may be inserted in the loop 804-805 to notify surgery staff, or to take other appropriate action, in the event that the limit changes to the joint controller 400 may not be made within a reasonable period of time.

In other words, according to the method described in reference to FIG. 8, the torque limit is changed when the actual torque is less in absolute value than both the current torque limit and the new prospective torque limit. It is to be appreciated that such a strategy guarantees the lack of discontinuities in the torque command and hence no jerk in the instrument motion.

Figure 9:
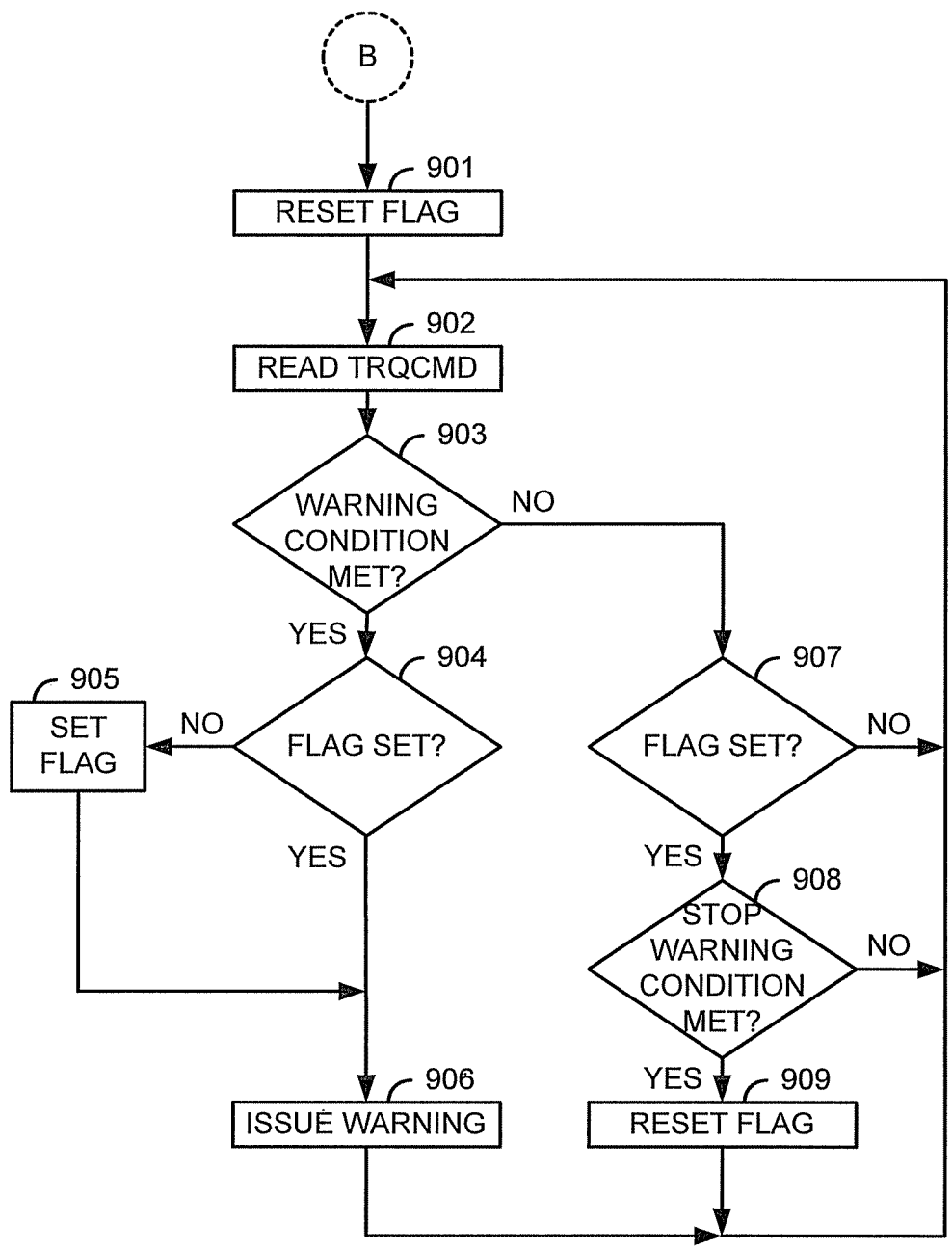
FIG. 9 illustrates a flow diagram of a method for issuing an excessive force warning to surgery staff when an actuator command is exceeding a threshold value for more than a programmed period of time, utilizing aspects of the present invention.

FIG. 9 illustrates, as an example, a flow diagram of a method for issuing an excessive force warning indication to surgery staff when an actuator command (e.g., the torque command TRQCMD) is exceeding a threshold value for more than a programmed period of time for a joint controller 400 of a slave manipulator. The method in this case is preferably triggered by changing of a control system parameter (e.g., after performance of 513 or 523 in FIG. 5) to adjust an adjustable characteristic of the slave manipulator.

In 901, a warning indication flag is reset. In 902, the torque command TRQCMD is read out or otherwise obtained from the control system processing calculations performed by the processor 102. In 903, a determination is made whether the torque command TRQCMD has been greater than a threshold value for more than a threshold period of time (e.g., 1.0 seconds).

If the determination in 903 is YES, then in 904, a determination is made whether the warning indication flag is set. Since on the first pass through 903 the warning indication flag is still reset (i.e., not set), the determination in 903 at this time is a NO. Consequently, in 905, the warning indication flag is set, and in 906, a warning is issued to surgery staff that excessive force is being commanded on the motor joints. Also, the slave manipulator is prevented at this time from responding to the excessive force command. Thereafter, on a subsequent pass through 903, the warning indication flag will be set so upon another YES determination in 903, the method skips setting the warning indication flag in 905, and in 906, repeats its warning to the surgery staff and continues to prevent the slave manipulator from responding to the excessive force command.

The warning issued in 906 may be auditory and/or visual in nature. For surgery staff at the patient site, the warning may be in the form of beeps emanating from the slave manipulator or it may be in the form of blinking or turning on of Light Emitting Diodes (LEDS) on the slave manipulator. For the surgeon who may be remotely performing the medical procedure through manipulation of input devices, the warning may be in the form of beeps emanating from a speaker in the Surgeon's console or a visual indication on either or both the display screen of the monitor in the Surgeon's console and the slave manipulator itself (such as turning on a red or yellow light emitting diode on the slave manipulator or its robotic arm assembly). Other well known warning indications may also be used, including vibrations on the input devices.

As a further refinement, when the left and right input devices 108, 109 are associated respectively with slave manipulators of robotic arm assemblies 128, 129, then an auditory warning issued for the slave manipulator of robotic arm assembly 128 (associated with the left input device 108) may be provided through a left speaker and an auditory warning issued for the slave manipulator of robotic arm assembly 129 (associated with the right input device 109) may be provided through a right speaker. The left and right speakers in this case may be provided in a stereophonic headset worn by the Surgeon or a stereophonic pair of speakers positioned near the Surgeon so as to minimize crosstalk and provide good left and right side feedback localization. Vibrations on the left and right input devices 108, 109 may also (or alternatively) be used as sensory warnings respectively for the slave manipulators associated with those input devices.

If the determination in 903 is NO, however, then in 907, a determination is made whether the warning indication flag is set or not. If no excessive force warning has been issued yet, then the warning indication flag is still reset from 901. In that case, the method returns to 902 to read a next-in-time torque command TRQCMD and proceed through the rest of the method. On the other hand, if an excessive force warning is currently pending, then the warning indication flag has been set in 905. In this case, the method proceeds to 908 where a determination is made whether the torque command TRQCMD has been less than the threshold value for more than a second threshold period of time (e.g., 0.1 seconds). If the determination in 908 is NO, then the method returns to 902 to read a next-in-time torque command TRQCMD and proceed through the rest of the method. On the other hand, if the determination in 908 is YES, then in 909, the warning indication flag is reset, the slave manipulator is no longer prevented from responding to the torque command TRQCMD, and the method returns to 902 to read a next-in-time torque command TRQCMD and proceed through the rest of the method.

Although the various aspects of the present invention have been described with respect to a preferred embodiment, it will be understood that the invention is entitled to full protection within the full scope of the appended claims.

We claim:

1. A method implemented by a processor for dynamically adjusting a stiffness of a slave manipulator coupleable to a medical device, the method comprising:
    the processor determining, during a medical procedure, whether the stiffness of the slave manipulator is to be adjusted by applying a set of expert rules stored in a memory, the set of expert rules using information of at least one of a functional type of the medical device and a current phase of the medical procedure; and
    conditioned upon the processor determining that the stiffness of the slave manipulator is to be adjusted by applying the set of expert rules, the processor dynamically adjusting, during the medical procedure, the stiffness of the slave manipulator, by automatically changing a gain according to a value stored along with the set of expert rules in the memory, wherein the gain is used within a control system for controlling movement of the slave manipulator.

2. The method according to claim 1, wherein the processor determining whether the stiffness is to be adjusted, comprises:
    the processor determining that the stiffness is to be adjusted if the functional type of the medical device is one aiming at delivering a controlled mechanical energy to an anatomic structure of a patient and the current phase of the medical procedure involves such delivery of mechanical energy by the medical device.

3. The method according to claim 2, wherein if the functional type of the medical device is of a first class of medical devices that deliver controlled mechanical energy to the anatomic structure, then the gain is to be adjusted so that induced movement of the medical device resulting from counter reactionary forces created during the delivery of mechanical energy to the anatomic structure is reduced.

4. The method according to claim 2, wherein if the functional type of the medical device is of a second class of medical devices that aims at stabilizing the anatomic structure, then the gain is to be adjusted so that the medical device is allowed limited movement when contacting the anatomic structure.

5. The method according to claim 1, wherein the processor determining whether the stiffness is to be adjusted, comprises:
    the processor determining that the stiffness is to be adjusted if the functional type of the medical device is one where the medical device is to be guided through or around an anatomic structure of a patient and the current phase of the medical procedure involves such guidance of the medical device.

6. The method according to claim 5, wherein the gain is to be adjusted so that induced movement of the medical device from external forces is reduced.

7. The method according to claim 1, wherein the processor determining whether the stiffness is to be adjusted, comprises:
    the processor determining that the stiffness is to be adjusted if the functional type of the medical device is one where the medical device is to control positioning of an anatomic structure in a patient and the current phase of the medical procedure involves such controlled positioning of the anatomic structure by the medical device.

8. The method according to claim 7, wherein if the medical device is in the process of controlling the position of the anatomic structure in the patient, then the gain is to be adjusted so as resist movement of the medical device by externally applied forces.

9. The method according to claim 7, wherein the functional type of the medical device is one that retracts and holds the anatomic structure during at least one phase of the medical procedure.

10. The method according to claim 7, wherein the functional type of the medical device is one that stabilizes the anatomic structure during at least one phase of the medical procedure.

11. The method according to claim 1, wherein the processor determining whether the stiffness is to be adjusted, comprises:
    the processor determining that the stiffness is to be adjusted if the functional type of the medical device is for suturing and the current phase of the medical procedure involves such suturing using the medical device.

12. The method according to claim 1, wherein the processor determining whether the stiffness is to be adjusted, comprises:
    the processor determining that the stiffness is to be adjusted if the functional type of the medical device is one where the medical device is used for ultrasound surface scanning and the current phase of the medical procedure involves such ultrasound surface scanning using the medical device.

13. The method according to claim 1, further comprising:
    the processor identifying an operative mode of the slave manipulator;
    wherein the criteria used for determining whether the stiffness is to be adjusted further includes the operative mode of the slave manipulator.

14. The method according to claim 13, wherein the operative mode comprises a locked mode wherein the slave manipulator is non-responsive to operator manipulation of the master manipulator and is held in place, and an unlocked mode wherein the slave manipulator is responsive to operator manipulation of the master manipulator; and wherein the processor determining whether the stiffness of the first slave manipulator is to be adjusted depends upon whether the operative mode is in the locked mode or the unlocked mode.

15. The method according to claim 14, wherein the gain is to be changed so that the stiffness of the slave manipulator in the locked mode is different than the stiffness of the slave manipulator in the unlocked mode.

16. The method according to claim 1, further comprising:
    the processor identifying the functional type of the medical device by electronically reading an identifier in a memory in the medical device.

17. The method according to claim 1, further comprising:
    the processor receiving an indication of the functional type of the medical device from a graphical user interface.

18. The method according to claim 1, further comprising:
    the processor receiving an indication of the current phase of the medical procedure from a graphical user interface.

19. The method according to claim 1, further comprising:
    the processor determining whether changing the gain would result in a motor command that exceeds a threshold value immediately following the changing the gain, wherein the motor command is generated by a first slave joint controller to drive a motor of the slave manipulator;

wherein the processor dynamically adjusting the stiffness of the slave manipulator comprises the processor changing the gain, which is used within the first slave joint controller, when the stiffness is to be adjusted and the motor command would not exceed the threshold value immediately following the changing the gain.

20. The method according to claim 19, wherein the processor determining whether changing the gain would result in the motor command exceeding the threshold value immediately following the change in the gain comprises:
- the processor determining the current motor command generated by the first slave joint controller using a current position error gain in the first slave joint controller;
- the processor determining a prospective motor command to be generated within the first slave joint controller immediately following changing the gain, which is used within the first slave joint controller, by changing the current position error gain to a new position error gain in the first slave joint controller; and
- the processor determining whether an absolute value of a difference between the current and the prospective motor command is greater than the threshold value.

21. The method of claim 1, further comprising:
- the processor receiving a slave manipulator command to move the medical device;
- the processor mapping the slave manipulator command to a plurality of slave joint position commands including a first slave joint position command, by using inverse kinematics of the slave manipulator; and
- the processor providing the first slave joint position command to a first slave joint controller, wherein the gain is used.

22. The method of claim 1, wherein the gain magnifies a feedback error in a first slave joint controller when the gain is increased, the feedback error determined as a difference between a current first slave joint position and a first slave joint position indicated by the first slave joint position command, and the gain positioned inside the first slave joint controller.

* * * * *